(12) United States Patent
Attaluri et al.

(10) Patent No.: US 10,395,176 B2
(45) Date of Patent: *Aug. 27, 2019

(54) DATA BASED TRUTH MAINTENANCE

(71) Applicant: International Business Machines Corporation, Armonk, NY (US)

(72) Inventors: Prabhakar Attaluri, Aurora, IL (US); Mickey Iqbal, Tucker, GA (US); Calvin D. Lawrence, Lithonia, GA (US); Matthew B. Trevathan, Roswell, GA (US)

(73) Assignee: International Business Machines Corporation, Armonk, NY (US)

( * ) Notice: Subject to any disclaimer, the term of this patent is extended or adjusted under 35 U.S.C. 154(b) by 882 days.

This patent is subject to a terminal disclaimer.

(21) Appl. No.: 15/010,498

(22) Filed: Jan. 29, 2016

(65) Prior Publication Data

US 2016/0147961 A1 May 26, 2016

Related U.S. Application Data

(63) Continuation of application No. 13/973,513, filed on Aug. 22, 2013, now Pat. No. 9,280,743, which is a
(Continued)

(51) Int. Cl.
*G06N 5/04* (2006.01)
*G06F 19/00* (2018.01)
(Continued)

(52) U.S. Cl.
CPC .............. *G06N 5/04* (2013.01); *G06F 19/00* (2013.01); *G06Q 50/24* (2013.01); *G16H 10/60* (2018.01); *G16H 50/20* (2018.01)

(58) Field of Classification Search
CPC .......... G06N 5/04; G16H 10/60; G16H 50/20; G06F 19/00; G06Q 50/24
See application file for complete search history.

(56) References Cited

U.S. PATENT DOCUMENTS 5,955,950 A 9/1999 Gallagher, III et al.
6,832,199 B1 12/2004 Kucek et al.
(Continued)

OTHER PUBLICATIONS

Falkenhainer, Brian. "Towards a general-purpose belief maintenance system." Machine Intelligence and Pattern Recognition. vol. 5. North-Holland, 1988. 125-131. (Year: 1988).*
(Continued)

*Primary Examiner* — Eric Nilsson
(74) *Attorney, Agent, or Firm* — Schmeiser, Olsen & Watts; Michael A. Petrocelli

(57) ABSTRACT

A truth maintenance method and system. The method includes receiving by a computer processor, health event data associated with heath care records for patients. The computer processor associates portions of the health event data with associated patients and related records in a truth maintenance system database. The computer processor derives first health related assumption data and retrieves previous health related assumption data derived from and associated with previous portions of previous health event data. The computer processor executes non monotonic logic with respect to the first health related assumption data and the previous health related assumption data. In response, the computer processor generates and stores updated first updated health related assumption data associated with the first health related assumption data and the previous health related assumption data.

19 Claims, 3 Drawing Sheets

Related U.S. Application Data continuation of application No. 12/888,459, filed on Sep. 23, 2010, now Pat. No. 8,538,903.

(51) Int. Cl.
*G06Q 50/24* (2012.01)
*G16H 10/60* (2018.01)
*G16H 50/20* (2018.01)

(56) References Cited

U.S. PATENT DOCUMENTS

| | | | |
|---|---|---|---|
| 7,378,967 B2 | 5/2008 | Sullivan et al. | |
| 7,447,670 B1* | 11/2008 | Chen | G06N 7/005 706/52 |
| 7,479,883 B2 | 1/2009 | Chiu | |
| 7,528,696 B2 | 5/2009 | Mickle et al. | |
| 7,538,678 B2 | 5/2009 | Jung et al. | |
| 8,116,430 B1 | 2/2012 | Shapiro et al. | |
| 8,494,999 B2 | 7/2013 | Attaluri et al. | |
| 8,538,903 B2 | 9/2013 | Attaluri et al. | |
| 9,280,743 B2 | 3/2016 | Attaluri et al. | |
| 2003/0198316 A1 | 10/2003 | Dewaele et al. | |
| 2004/0152952 A1 | 8/2004 | Gotlib et al. | |
| 2005/0007249 A1 | 1/2005 | Eryurek et al. | |
| 2005/0209886 A1 | 9/2005 | Corkern | |
| 2006/0049250 A1 | 3/2006 | Sullivan et al. | |
| 2007/0194939 A1 | 8/2007 | Alvarez et al. | |
| 2008/0010225 A1 | 1/2008 | Gonsalves et al. | |
| 2008/0033894 A1 | 2/2008 | Steck et al. | |
| 2008/0055085 A1 | 3/2008 | Samboursky et al. | |
| 2008/0122622 A1 | 5/2008 | Archer et al. | |
| 2008/0275731 A1 | 11/2008 | Rao et al. | |
| 2009/0002163 A1 | 1/2009 | Farrington et al. | |
| 2009/0085738 A1 | 4/2009 | Darianian et al. | |
| 2009/0089239 A1* | 4/2009 | Herrera | G06N 5/022 706/59 |
| 2009/0177495 A1* | 7/2009 | Abousy | G16H 50/20 705/3 |
| 2009/0326981 A1 | 12/2009 | Karkanias et al. | |
| 2010/0056877 A1 | 3/2010 | Fein et al. | |
| 2010/0075353 A1 | 3/2010 | Heaton | |
| 2010/0114781 A1 | 5/2010 | Kassas | |
| 2010/0179391 A1 | 7/2010 | Quintanar, II et al. | |
| 2010/0205739 A1 | 8/2010 | Gallant et al. | |
| 2010/0324927 A1* | 12/2010 | Tinsley | G06F 19/325 705/2 |
| 2012/0075067 A1 | 3/2012 | Attaluri et al. | |
| 2012/0078835 A1 | 3/2012 | Attaluri et al. | |
| 2012/0203419 A1 | 8/2012 | Tucker et al. | |
| 2013/0275148 A1 | 10/2013 | Attaluri et al. | |
| 2013/0282644 A1 | 10/2013 | Attaluri et al. | |
| 2013/0346358 A1 | 12/2013 | Attaluri et al. | |

OTHER PUBLICATIONS

Amendment filed Dec. 29, 2014 in response to Office Action (dated Oct. 1, 2014) for U.S. Appl. No. 13/445,299, filed Apr. 12, 2012.
Amendment filed Dec. 31, 2015 in response to Office Action (dated Oct. 8, 2015) for U.S. Appl. No. 13/917,718, filed Jun. 14, 2013.
Final Office Action (dated Feb. 26, 2015) for U.S. Appl. No. 13/445,299, filed Apr. 12, 2012.
Office Action (dated Oct. 1, 2014) for U.S. Appl. No. 13/445,299, filed Apr. 12, 2012.
Office Action (dated Oct. 8, 2015) for U.S. Appl. No. 13/917,718, filed Jun. 14, 2013.
Preliminary Amendment and Request for Continued Examination filed May 20, 2015 in response to Final Office Action (dated Feb. 26, 2015) for U.S. Appl. No. 13/445,299, filed Apr. 12, 2012.
Rolim et al.; A Cloud Computing Solution for Patient's Data Collection in Health Care Institutions; Second International Conference on eHealth, Telemedicine, and Social Medicine; Etelemed '10, 2010; Feb. 10-16, 2010; pp. 95-99.
Hagel et al.; Cloud Computing—Storms on the Horizon; Deloitte Center for the Edge; Apr. 20, 2010; 20 pages.
Fahy, Joe; UPMC testing 'smart' rooms; Pittsburgh Post-Gazette; URL: http://www.post-gasette.com/pg/08016/849476-53.stm; retrieved from the Internet Jun. 9, 2011; 4 pages.
Unknown (Posted by Editor); Introducing Smart Patient Rooms; Empowering Healthcare Practice and Management blog; URL: http://healthcaremanagementblog.com/smart-patient-rooms/; retrieved from the Internet Jun. 6, 2011; 4 pages.
Office Action (dated Aug. 1, 2012) for U.S. Appl. No. 12/888,459, filed Sep. 23, 2010.
Amendment filed Oct. 30, 2012 in response to Office Action (dated Aug. 1, 2012) for U.S. Appl. No. 12/888,459, filed Sep. 23, 2010.
Final Office Action (dated Feb. 13, 2013) for U.S. Appl. No. 12/888,459, filed Sep. 23, 2010.
Amendment After Final filed Apr. 1, 2013 in response to Final Office Action (dated Feb. 13, 2013) for U.S. Appl. No. 12/888,459, filed Sep. 23, 2010.
Notice of Allowance (dated May 9, 2013) for U.S. Appl. No. 12/888,459, filed Sep. 23, 2010.
Office Action (dated Aug. 14, 2012) for U.S. Appl. No. 12/888,476, filed Sep. 23, 2010.
Amendment filed Nov. 9, 2012 in response to Office Action (dated Aug. 14, 2012) for U.S. Appl. No. 12/888,476, filed Sep. 23, 2010.
Final Office Action (dated Jan. 4, 2013) for U.S. Appl. No. 12/888,476, filed Sep. 23, 2010.
Amendment After Final filed Feb. 19, 2013 in response to Final Office Action (dated Jan. 4, 2013) for U.S. Appl. No. 12/888,476, filed Sep. 23, 2010.
Notice of Allowance (dated Mar. 15, 2013) for U.S. Appl. No. 12/888,476, filed Sep. 23, 2010.
Antonelli, G Aldo, Non-monotonic Logic, The Stanford Encyclopedia of Philosophy (Summer 2010 Edition), Edward N. Zalta (ed.) URL: http://plato.stanford.edu/archives/sum2010/entries/logic-nonmonotic/; retrieved from the Internet Jul. 30, 2012; 19 pages.
El-Zahary et al.; Diagnostic Expert System Using Non-monotonic Reasoning; Expert Systems with Applications, vol. 23; 2002; 8 pages.
Office Action (dated Feb. 12, 2016) for U.S. Appl. No. 13/445,299, filed Apr. 12, 2012.
Notice of Allowance (dated Feb. 19, 2016) for U.S. Appl. No. 13/917,718, filed Jun. 14, 2013.
U.S. Appl. No. 15/075,351, filed Mar. 21, 2016.

* cited by examiner

DATA BASED TRUTH MAINTENANCE

This application is a continuation application claiming priority to Ser. No. 13/973,513 filed Aug. 22, 2013 which is a continuation application claiming priority to Ser. No. 12/888,459 filed Sep. 23, 2010 now U.S. Pat. No. 8,538,903 issued Sep. 17, 2013 and is related to application Ser. No. 12/888,476 filed on Sep. 23, 2010.

FIELD

The present invention relates to a method and associated system for generating health related assumptions based on events retrieved from data sources.

BACKGROUND

Generating predictions from specific data retrieved from various sources typically comprises an inefficient process with little flexibility. Predictions are typically generated without any regard to additional data. Predictions generated without any regard to additional data may result in inaccurate predictions.

SUMMARY

The present invention provides a method comprising: receiving, by a computer processor of a computing device from a plurality of data sources, first health event data associated with a first plurality of heath care records associated with a plurality of patients, the computer processor controlling a cloud hosted mediation system comprising an inference engine software application, a truth maintenance system database, and non monotonic logic; associating, by the computer processor, portions of the first health event data with associated patients of the plurality of patients; associating, by the computer processor, the portions of the first health event data with related records in the truth maintenance system database; deriving, by the computer processor executing the inference engine software application, first health related assumption data associated with each portion of the portions of the first health event data; retrieving, by the computer processor from the truth maintenance system database, previous health related assumption data derived from and associated with previous portions of previous health event data retrieved from the plurality of data sources, the previous health related assumption data derived at a time differing from a time of the deriving, the previous health related event data associated with previous health related events occurring at a different time from the first health event data; executing, by the computer processor, the non monotonic logic with respect to the first health related assumption data and the previous health related assumption data; generating, by the computer processor executing the non monotonic logic and the inference engine software application, first updated health related assumption data associated with the first health related assumption data and the previous health related assumption data; and storing, by the computer processor in the truth maintenance system database the first health related assumption data and the first updated health related assumption data.

The present invention provides a computer program product, comprising a computer readable storage medium having a computer readable program code embodied therein, the computer readable program code comprising an algorithm that when executed by a computer processor implements a method within a computing device, the method comprising: receiving, by the computer processor from a plurality of data sources, first health event data associated with a first plurality of heath care records associated with a plurality of patients, the computer processor controlling a cloud hosted mediation system comprising an inference engine software application, a truth maintenance system database, and non monotonic logic; associating, by the computer processor, portions of the first health event data with associated patients of the plurality of patients; associating, by the computer processor, the portions of the first health event data with related records in the truth maintenance system database; deriving, by the computer processor executing the inference engine software application, first health related assumption data associated with each portion of the portions of the first health event data; retrieving, by the computer processor from the truth maintenance system database, previous health related assumption data derived from and associated with previous portions of previous health event data retrieved from the plurality of data sources, the previous health related assumption data derived at a time differing from a time of the deriving, the previous health related event data associated with previous health related events occurring at a different time from the first health event data; executing, by the computer processor, the non monotonic logic with respect to the first health related assumption data and the previous health related assumption data; generating, by the computer processor executing the non monotonic logic and the inference engine software application, first updated health related assumption data associated with the first health related assumption data and the previous health related assumption data; and storing, by the computer processor in the truth maintenance system database the first health related assumption data and the first updated health related assumption data.

The present invention provides a computing system comprising a computer processor coupled to a computer-readable memory unit, the memory unit comprising instructions that when executed by the computer processor implements a method comprising: receiving, by the computer processor from a plurality of data sources, first health event data associated with a first plurality of heath care records associated with a plurality of patients, the computer processor controlling a cloud hosted mediation system comprising an inference engine software application, a truth maintenance system database, and non monotonic logic; associating, by the computer processor, portions of the first health event data with associated patients of the plurality of patients; associating, by the computer processor, the portions of the first health event data with related records in the truth maintenance system database; deriving, by the computer processor executing the inference engine software application, first health related assumption data associated with each portion of the portions of the first health event data; retrieving, by the computer processor from the truth maintenance system database, previous health related assumption data derived from and associated with previous portions of previous health event data retrieved from the plurality of data sources, the previous health related assumption data derived at a time differing from a time of the deriving, the previous health related event data associated with previous health related events occurring at a different time from the first health event data; executing, by the computer processor, the non monotonic logic with respect to the first health related assumption data and the previous health related assumption data; generating, by the computer processor executing the non monotonic logic and the inference engine software application, first updated health related assumption data associated with the first health related assumption data and the previous health related assumption data; and storing, by the computer processor in the truth maintenance system database, the first health related assumption data and the first updated health related assumption data.

The present invention advantageously provides a simple method and associated system capable of generating predictions from data retrieved from various sources.

DETAILED DESCRIPTION

Figure 1:
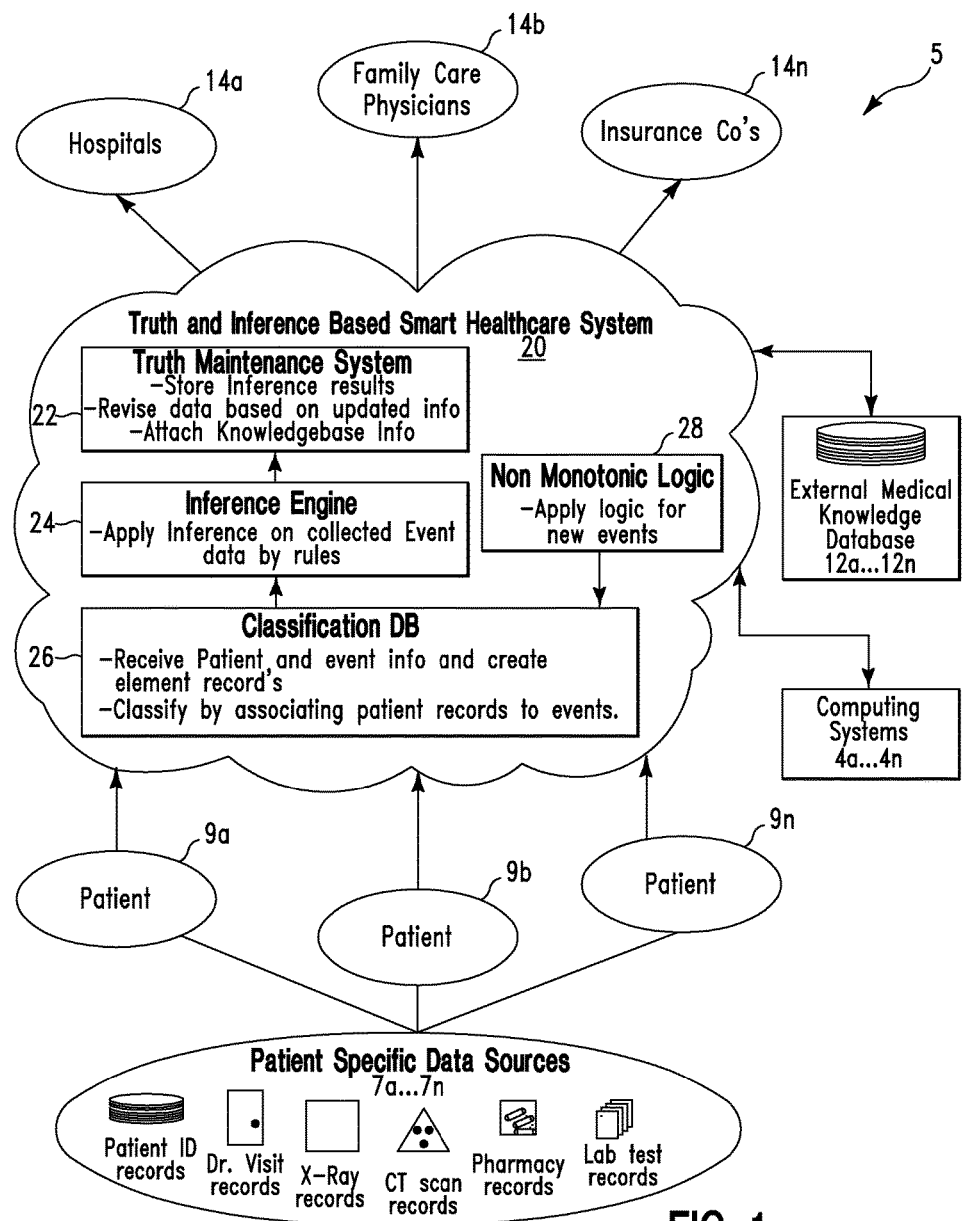
FIG. 1 illustrates a system for generating revisable assumptions based on applying monotonic logic to healthcare data, in accordance with embodiments of the present invention.

FIG. 1 illustrates a system 5 for generating revisable assumptions based on applying monotonic logic to healthcare related data, in accordance with embodiments of the present invention. System 5 enables a method for providing a truth maintenance system based on retrieving information via patient specific data sources 7a . . . 7n and external medical knowledge databases 12a . . . 12n. System 5 provides a smart cloud based IT application for receiving, filtering, and analyzing patient data from multiple sources received at different intervals stored in a classification database and managed with a truth maintenance based logical algorithm. Dashboard views of the multiple assertions may be generated based on new or updated information received.

System 5 of FIG. 1 comprises health care provider systems 14a . . . 14n, patient specific data sources 7a . . . 7n (e.g., patient ID records, physician visit records, X-ray records, CT scan records, pharmacy records, lab test records, etc), and external medical knowledge databases 12a . . . 12n connected to a cloud hosted mediation system 20 controlled by computing systems 4a . . . 4n. Although system 5 is described with respect to retrieving information via patient specific data sources 7a . . . 7n and external medical knowledge databases 12a . . . 12n, note that information may be retrieved via any type of database or receiver/transceivers (e.g., satellite receiver/transceivers, any type of wireless receiver/transceivers, etc). Additionally, the information may be retrieved via a combination of different types of receiver/transceivers and/or databases. Cloud hosted mediation system 20 is controlled by multiple computers and network devices (i.e., computing systems 4a . . . 4n) all running in 100% virtualized mode with virtual machines running application software for different functions. Cloud hosted mediation system 20 utilizes a cloud infrastructure instantiating an application based on a consumption based pay as you go delivery model. Patient specific data sources 7a . . . 7n, external medical knowledge databases 12a . . . 12n, and health care provider systems 14a . . . 14n are integrated into cloud hosted mediation system 20 using secure network protocols. Cloud hosted mediation system 20 comprises an Inference Engine (IE) 24 (software application) and advanced non monotonic logic 28 (i.e., executed as a software application) stored and managed in by a truth maintenance system (TMS) 22. TMS 22 comprises a data model. Classified event data (i.e., retrieved from patient specific data sources 7a . . . 7n and external medical knowledge databases 12a . . . 12n) is inputted into inference engine 24 to derive plausible answers by applying rule based reasoning to the classified event data. TMS 22 stores previously retrieved classified event data and applies new knowledge information to stored updated data (i.e., stored in classification database 26). I.E. 24 derives plausible answers from retrieved evidence that is continuously being collected from multiple information sources (e.g., patient specific data sources 7a . . . 7n, external medical knowledge databases 12a . . . 12n, etc). A subset of plausible answers for some forms of evidence may be stored in a database associated with IE 24. Additionally, new plausible answers are added to the database (i.e., continuously) based on evidence collection. IE 24, TMS 22, and non monotonic logic 28 in combination provide classified medical/patient related data analysis from multiple patient specific data sources 7a . . . 7n and external medical knowledge databases 12a . . . 12n thereby improving outcomes and accuracy before health care provider systems 14a . . . 14n retrieve the outcomes.

System 5 provides a cloud hosted smart healthcare system with IE 24 and an advanced non-monotonic logic processing system (i.e., and non monotonic logic 28) that is stored and managed along with TMS 22. Classified patient data from multiple sources (e.g., patient specific data sources 7a . . . 7n) is processed by IE 24 in order to derive plausible answers by applying rule based reasoning. TMS 22 retains past inferred data and applies new knowledge information (e.g., new lab reports, etc) to store updated data. IE 24, TMS 22, and non-monotonic logic 28 combined together provide classified and analyzed diagnostic assertions thereby improving health outcomes and accuracy. System 5 is maintained in a pay-by-usage cloud environment. Cloud hosted service is further integrated into external medical knowledge databases 12a . . . 12n (e.g., DX plain, FDA knowledgebase, etc) to provide comprehensive informational dashboard views and reports (e.g., comprising information such as medicines that address an issue) suitable for a patient profile. Physicians may use the reports for diagnostic decision making. System 5 combines advanced artificial intelligence approaches (for patient data from multiple sources) integrated with a medical knowledgebase and delivered in a cloud based usage model. System 5 provides a knowledge based artificial intelligence system combined with a TMS based system and non-monotonic logic reasoning for predicting health outcomes for patients. Inferences are applied to patient information arriving at different time intervals and TMS assertions are updated with plausibility values based on the new events.

Non monotonic logic 28 provides non monotonic reasoning with respect to system 5. Non monotonic reasoning comprises an approach in which axioms and/or rules of inference are extended to make it possible to reason with incomplete information. Additionally, non monotonic reasoning allows for reasoning that allows system 5 to back track a reasoning sequence and make an alternate decision. The following implementation example 1 describes non monotonic reasoning as follows:

Example 1

In example 1 a person looks outside his/her house to see that it is currently not raining and that the sky is clear (i.e., evidence 1). Therefore the person determines that there is very little chance of rain. The person decides to walk to work without taking an umbrella (i.e., action 1). After taking a few steps outside the house the person notices that dark clouds are forming (i.e. evidence 2). Additionally, the person notices bolt of lightning in the distance (i.e., evidence 3) and determines that there is currently a very high likelihood of rain. Based on this new information, the person walks back to the house (i.e., action 2) and picks up and opens an umbrella and then continues to walk to work. (i.e., action 3). The aforementioned example demonstrates that a person believes in one outcome (such as there is very little chance of rain) based on evidence 1 and decides to take on a course of action (i.e., action 1) based on an initial belief. As new facts (i.e., evidence 2 and 3) become known which appear to contradict the initial belief the person develops a new belief (such as there is a very high likelihood of rain) and based on the new updated belief, the person backtracks on his/her initial decision and decides to take another different set of actions (i.e., actions 2 and 3).

Non monotonic logic in combination with a Dempster Shafer (D-S) theory is used to generate possible outcomes. In system 5, the utility of probability theory for modeling reasoning with uncertainty is limited by a lack of sufficient data to accurately estimate prior and conditional probabilities required in using Bayes' rule. D-S theory sidesteps the requirement for this data. D-S theory accepts an incomplete probabilistic model without prior or conditional probabilities. Given the incompleteness of the model, D-S theory does not answer arbitrary probabilistic questions. Rather than estimating the probability of a hypothesis, D-S theory uses belief intervals to estimate how close evidence is to determining a truth of a hypothesis. A non monotonic approach in accumulating evidence comprises provisions for retracting evidence and the D-S approach may be used together with a non monotonic approach to determine how much belief should be assigned to each set of evidence. System 5 computes a probability (i.e., a percentage) for each assumption as new evidence is retrieved. System 5 enables a programmed implementation (e.g., via a software application) the D-S theory of Mathematical evidence. The use of the D-S approach requires inference engine 24 to deduce belief functions. TMS 22 comprises a system/program that provides a symbolic mechanism for identifying a set of assumptions needed to assemble desired proofs so that when probabilities of the assumptions are assigned. TMS 22 may be used as a symbolic engine for computing degrees of belief sought by the D-S theory. Additionally, TMS 22 handles an effect of retracting assumptions that have been invalidated by evidence. TMS additionally keeps track of multiple plausible sets of assertions which may coexist in the absence of complete knowledge. The following example 2 describes an implementation example (i.e., with respect to example 1 comprising the rain/no rain example) for implementing TMS 22.

Example 2

In example 2, a belief there is "little chance of rain" (as in example 1) is maintained in TMS 22 as one set of assumptions (i.e., set 1). A belief that "there is a very high likelihood of rain" (as in example 1) is maintained in TMS 22 as second set of assumptions (i.e., set 2). Set 2 is favored with higher belief as compared to set 1. As time passes, the person notices that the clouds start to fade away and it becomes very sunny outside (i.e., evidence 4). The person checks a weather forecast using a portable device weather application and finds there is very little possibility of rain (i.e., evidence 5). The person folds the umbrella and continues to walk to work. (i.e., action 4). Based on the aforementioned processing, two new evidences are generated which result in supporting assumptions in set 1. Therefore, assumptions set 1 are now more highly favored instead of assumptions in set 2.

The following implementation example 3 enabled by system 5 of FIG. 1 comprises applying non monotonic reasoning in conjunction with TMS 22 and the D-S theory of mathematical evidence in order to explore multiple possible outcomes at a same time (or in parallel) while allowing back-tracking in real time thereby recommending different outcomes as new evidence becomes known.

Example 3

Example 3 comprises a patient medical diagnosis scenario. In a first step, diagnosis related data associated with multiple patients is generated by different database feeders (e.g., doctor's offices, diagnostic centers, hospitals, etc). The diagnosis related data may include patient specific details such as, inter alia, lab reports, CT scan reports, physician comments from patient visits, etc. The diagnosis related data is fed directly into system 5 which sorts the diagnosis related data based on patient ids and associates the diagnosis related data to an existing record (or adds it as a new record). System 5 associates related events together and loads the associated events into a classification DB (e.g., classification DB 26). IE 24 crawls through classified data (i.e., facts) stored in the classification DB and derives assumption type answers (e.g., set1). Two pieces of evidence (i.e., of set 1) support the fact that a patient A has medical condition of xx with a plausibility of 30% and 3 pieces of evidence generated (i.e., set 2) supports the fact that patient A has a medical condition yy with a plausibility of 50%. Both sets of beliefs (i.e., set 1 and set 2) are processed using the D-S theory of evidence and which illustrates that one belief is higher than the other. The two sets (set 1 and set 2) of beliefs established are stored in TMS 22. Based on the aforementioned processing, system 5 generates an initial recommendation based on set 2 and its associated higher belief assignment by the D-S theory application. As time passes the diagnosis related data is updated with new information as multiple new events and related evidence is generated by the database feeders. This additional data is fed into system 5 which logs the events and associates them together inside the classification DB. IE 24 crawls through the classified data (facts) stored in the database and derives assumption type answers. For example, five different events and associated evidence support the fact that patient A has the medical condition yy with a plausibility of 30% and only 2 pieces of evidence generated support the fact that patient A has the medical condition xx with a plausibility of 10%). The sets of beliefs established by the previous step and assigned using D-S theory are used to update the belief in the set 1 and set 2 which are being stored in TMS 22. As a result of this update in the D-S theory belief functions, set 1 now states that patient A has medical condition yy with a probability of 80% and set2 now says that patient A has medical condition xx with probability of 10%. System 5 generates a new recommendation based on set 1 and its associated higher belief assignment by the D-S theory application. The new recommendation is correlated with a patients existing medical records and with an external medical knowledgebase for possible treatment options presented in dashboard type views to a healthcare provider (i.e., this is example of non-monotonic reasoning where a decision has been reversed as new information is uncovered). IE 24, TMS 22, the D-S theory application, internal knowledgebase, integration to external knowledgebase, and dashboard user interface are all implemented on cloud based pay as you go model transparent to an end user.

Figure 2:
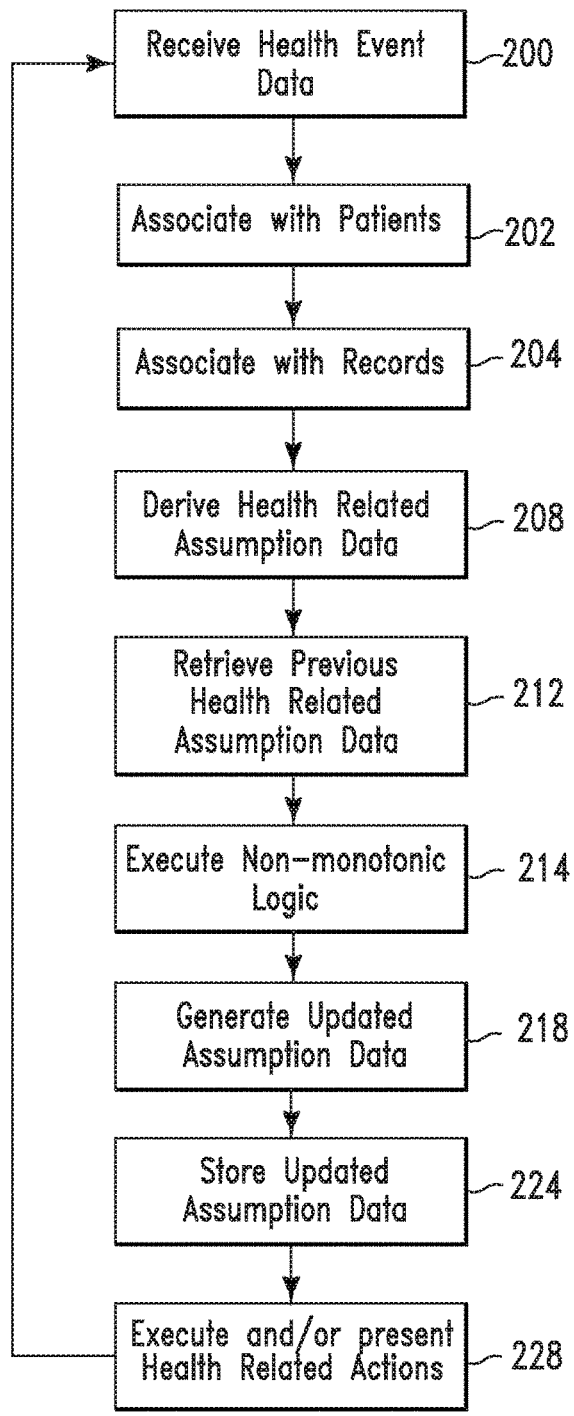
FIG. 2 illustrates an algorithm used by the system of FIG. 1 for generating revisable assumptions based on applying monotonic logic to healthcare data, in accordance with embodiments of the present invention.

FIG. 2 illustrates an algorithm used by system 5 of FIG. 1 for generating revisable assumptions based on applying monotonic logic to healthcare related data, in accordance with embodiments of the present invention. In step 200, a computer processor of a computing device (e.g., computing device 10 in FIG. 1) receives (from data sources such as patient specific data sources 7a . . . 7n in FIG. 1) health event data associated with heath care records associated with patients. The computer processor controls a cloud hosted mediation system (e.g., cloud hosted mediation system 20 of FIG. 1) comprising an inference engine software application (e.g., inference engine software application 24 of FIG. 1), a truth maintenance system database (e.g., truth maintenance system database 22 of FIG. 1), and non monotonic logic (e.g., non monotonic logic 28 of FIG. 1). In step 202, the computer processor associates portions of the health event data with associated patients. In step 204, the computer processor associates the portions of the health event data with related medical records in a truth maintenance system database. In step 208, the computer processor (i.e., executing the inference engine software application) derives health related assumption data associated with each portion of the health event data. In step 212, computer processor retrieves (i.e., from the truth maintenance system database) previous health related assumption data derived from and associated with previous portions of previous health event data retrieved from the data sources. The previous health related assumption data derived at a time differing from a time of deriving the health related assumption data in step 208. The previous health related event data is associated with previous health related events occurring at a different time from the health events received in step 200. In step 214, the computer processor executes the non monotonic logic with respect to the health related assumption data and the previous health related assumption data. The non monotonic logic may be executed as a software program. In step 218, the computer processor generating (i.e., in response to executing the non monotonic logic and the inference engine software application) updated health related assumption data associated with the health related assumption data and the previous health related assumption data. In step 224, the computer processor stores (i.e., in the truth maintenance system database) the health related assumption data and the updated health related assumption data. In step 228, the computer processor executes (i.e., based on the updated health related assumption data) a health related action associated with the patients. The actions may include, inter alia, implementing a pay by usage cloud metering model and presenting the actions to hospitals, physicians, insurance companies, etc.

Figure 3:
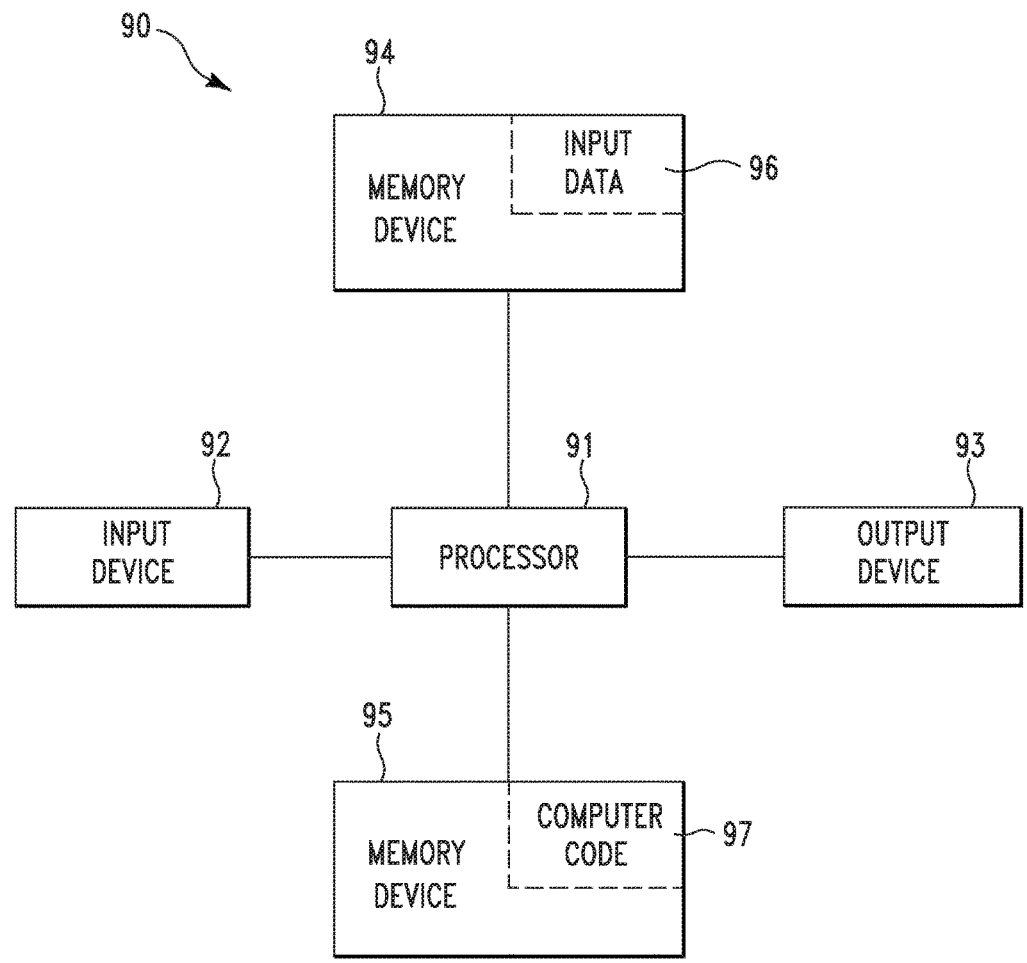
FIG. 3 illustrates a computer apparatus used for generating revisable assumptions based on applying monotonic logic to healthcare data, in accordance with embodiments of the present invention.

FIG. 3 illustrates a computer apparatus 90 (e.g., computing systems 4a . . . 4n of FIG. 1) used for generating revisable heath related assumptions based on applying monotonic logic to healthcare related data, in accordance with embodiments of the present invention. The computer system 90 comprises a processor 91, an input device 92 coupled to the processor 91, an output device 93 coupled to the processor 91, and memory devices 94 and 95 each coupled to the processor 91. The input device 92 may be, inter alia, a keyboard, a software application, a mouse, etc. The output device 93 may be, inter alia, a printer, a plotter, a computer screen, a magnetic tape, a removable hard disk, a floppy disk, a software application, etc. The memory devices 94 and 95 may be, inter alia, a hard disk, a floppy disk, a magnetic tape, an optical storage such as a compact disc (CD) or a digital video disc (DVD), a dynamic random access memory (DRAM), a read-only memory (ROM), etc. The memory device 95 includes a computer code 97. The computer code 97 includes algorithms (e.g., the algorithm of FIG. 2) for generating revisable heath related assumptions based on applying monotonic logic to healthcare related data. The processor 91 executes the computer code 97. The memory device 94 includes input data 96. The input data 96 includes input required by the computer code 97. The output device 93 displays output from the computer code 97. Either or both memory devices 94 and 95 (or one or more additional memory devices not shown in FIG. 3) may comprise the algorithm of FIG. 2 and may be used as a computer usable medium (or a computer readable medium or a program storage device) having a computer readable program code embodied therein and/or having other data stored therein, wherein the computer readable program code comprises the computer code 97. Generally, a computer program product (or, alternatively, an article of manufacture) of the computer system 90 may comprise the computer usable medium (or said program storage device).

Still yet, any of the components of the present invention could be created, integrated, hosted, maintained, deployed, managed, serviced, etc. by a service provider who offers to generate revisable heath related assumptions based on applying monotonic logic to healthcare related data. Thus the present invention discloses a process for deploying, creating, integrating, hosting, maintaining, and/or integrating computing infrastructure, comprising integrating computer-readable code into the computer system 90, wherein the code in combination with the computer system 90 is capable of performing a method for generating revisable heath related assumptions based on applying monotonic logic to healthcare related data. In another embodiment, the invention provides a method that performs the process steps of the invention on a subscription, advertising, and/or fee basis. That is, a service provider, such as a Solution Integrator, could offer to generate revisable heath related assumptions based on applying monotonic logic to healthcare related data. In this case, the service provider can create, maintain, support, etc. a computer infrastructure that performs the process steps of the invention for one or more customers. In return, the service provider can receive payment from the customer(s) under a subscription and/or fee agreement and/or the service provider can receive payment from the sale of advertising content to one or more third parties.

While FIG. 3 shows the computer system 90 as a particular configuration of hardware and software, any configuration of hardware and software, as would be known to a person of ordinary skill in the art, may be utilized for the purposes stated supra in conjunction with the particular computer system 90 of FIG. 3. For example, the memory devices 94 and 95 may be portions of a single memory device rather than separate memory devices.

While embodiments of the present invention have been described herein for purposes of illustration, many modifications and changes will become apparent to those skilled in the art. Accordingly, the appended claims are intended to encompass all such modifications and changes as fall within the true spirit and scope of this invention. All descriptions of methods and processes comprising steps herein are not limited to any specific order for performing the steps.

The invention claimed is:

1. A method comprising:

receiving, by a computer processor of a computing device from a plurality of data sources, first health event data associated with a first plurality of heath care records associated with a plurality of patients, said computer processor controlling a cloud hosted mediation system comprising an inference engine software application, a truth maintenance system database, and non monotonic logic, wherein said non monotonic logic comprises code for enabling a Dempster Shafer theory;

deriving, by said computer processor executing said inference engine software application, first health related assumption data associated with each portion of portions of said first health event data associated with associated patients of said plurality of patients and related records in said truth maintenance system database, wherein said first health related assumption data comprises multiple sets of assumptions associated with said plurality of patients, wherein each set of said multiple sets comprises assumed medical conditions and an associated plausibility percentage value, wherein at least two sets of said multiple sets is associated with each patient of set plurality of patients, wherein a first set of said multiple sets comprises evidence supporting a first fact indicating that a first patient of said plurality of patients has a first medical condition of said assumed medical conditions with a first plausibility percentage value, wherein a second set of said multiple sets comprises evidence supporting a second fact indicating that said first patient has a second medical condition of said assumed medical conditions with a second plausibility percentage value, wherein said first medical condition differs from said second medical condition, and wherein said first plausibility percentage value differs from said second plausibility percentage value;

determining, by said computer processor, based on results of executing the Dempster Shafer theory with respect to said first set and said second set, that said first set comprises a higher belief assignment value than said second set;

generating, by said computer processor based on results of said determining, said deriving and said first executing, an initial diagnosis and treatment recommendation for said first patient, said initial diagnosis and treatment recommendation associated with said first set;

retrieving, by said computer processor from said truth maintenance system database, previous health related assumption data derived from and associated with previous portions of previous health event data retrieved from said plurality of data sources, said previous health related assumption data derived at a time differing from a time of said deriving, said previous health related event data associated with previous health related events occurring at a different time from said first health event data;

additionally executing, by said computer processor executing said non monotonic logic, the Dempster Shafer theory with respect to said first set, said second set, said first patient, and said previous health related assumption data;

modifying, by said computer processor based on results of said additionally executing, said first plausibility percentage value of said first set and said second plausibility percentage value of said second set;

determining, by said computer processor, based on results of said additionally executing and said modifying, that said second set comprises a higher belief assignment value than said first set;

generating, by said computer processor based on said results of said additionally executing and said modifying, an updated diagnosis and treatment recommendation for said first patient; and generating, by said computer processor executing said non monotonic logic and said inference engine software application, first updated health related assumption data associated with said first health related assumption data and said previous health related assumption data, wherein said previous health related assumption data, said first health related assumption data, and said first updated health related assumption data each comprise assumptions associated with detected medical conditions of said plurality of patients.

2. The method of claim 1, further comprising:

executing, by said computer processor based on said first updated health related assumption data, health related actions associated with said plurality of patients.

3. The method of claim 2, wherein said health related actions comprise treatment options for said plurality of patients.

4. The method of claim 3, wherein said health related actions comprises implementing a pay by usage cloud metering model associated with said plurality of patients.

5. The method of claim 2, further comprising:

transmitting, by said computer processor to a plurality of health care providers, data describing said health related actions associated with said plurality of patients.

6. The method of claim 1, wherein said previous health related assumption data, said first health related assumption data, and said first updated health related assumption data each comprise assumptions associated with said plurality of patients.

7. The method of claim 1, wherein said generating first updated health related assumption data comprises retracting portions of said first health related assumption data and said previous health related assumption data.

8. The method of claim 7, further comprising:

retrieving, by said computer processor, historical patient data and treatment options data;

after said retracting, associating by said computer processor, said first updated health related assumption data with said historical patient data and said treatment options data;

generating, by said computer processor, health related recommendations associated with said plurality of patients; and presenting, by said computer processor via a dashboard view on a display device, said health related recommendations.

9. The method of claim 8, wherein said health related recommendations comprise treatment options for said plurality of patients.

10. The method of claim 1, further comprising:

providing at least one support service for at least one of creating, integrating, hosting, maintaining, and deploying computer-readable code in said computing system, wherein the code in combination with the computing system is capable of performing the method of claim 1.

11. A computer program product, comprising a non-transitory computer readable memory device storing a computer readable program code, said computer readable program code comprising an algorithm that when executed by a computer processor implements a method within a computing device, said method comprising:

receiving, by said computer processor from a plurality of data sources, first health event data associated with a first plurality of heath care records associated with a plurality of patients, said computer processor controlling a cloud hosted mediation system comprising an inference engine software application, a truth maintenance system database, and non monotonic logic, wherein said non monotonic logic comprises code for enabling a Dempster Shafer theory;

deriving, by said computer processor executing said inference engine software application, first health related assumption data associated with each portion of portions of said first health event data associated with associated patients of said plurality of patients and related records in said truth maintenance system database, wherein said first health related assumption data comprises multiple sets of assumptions associated with said plurality of patients, wherein each set of said multiple sets comprises assumed medical conditions and an associated plausibility percentage value, wherein at least two sets of said multiple sets is associated with each patient of set plurality of patients, wherein a first set of said multiple sets comprises evidence supporting a first fact indicating that a first patient of said plurality of patients has a first medical condition of said assumed medical conditions with a first plausibility percentage value, wherein a second set of said multiple sets comprises evidence supporting a second fact indicating that said first patient has a second medical condition of said assumed medical conditions with a second plausibility percentage value, wherein said first medical condition differs from said second medical condition, and wherein said first plausibility percentage value differs from said second plausibility percentage value;

determining, by said computer processor, based on results of executing the Dempster Shafer theory with respect to said first set and said second set, that said first set comprises a higher belief assignment value than said second set;

generating, by said computer processor based on results of said determining, said deriving and said first executing, an initial diagnosis and treatment recommendation for said first patient, said initial diagnosis and treatment recommendation associated with said first set;

retrieving, by said computer processor from said truth maintenance system database, previous health related assumption data derived from and associated with previous portions of previous health event data retrieved from said plurality of data sources, said previous health related assumption data derived at a time differing from a time of said deriving, said previous health related event data associated with previous health related events occurring at a different time from said first health event data;

additionally executing, by said computer processor executing said non monotonic logic, the Dempster Shafer theory with respect to said first set, said second set, said first patient, and said previous health related assumption data;

modifying, by said computer processor based on results of said additionally executing, said first plausibility percentage value of said first set and said second plausibility percentage value of said second set;

determining, by said computer processor, based on results of said additionally executing and said modifying, that said second set comprises a higher belief assignment value than said first set;

generating, by said computer processor based on said results of said additionally executing and said modifying, an updated diagnosis and treatment recommendation for said first patient; and generating, by said computer processor executing said non monotonic logic and said inference engine software application, first updated health related assumption data associated with said first health related assumption data and said previous health related assumption data, wherein said previous health related assumption data, said first health related assumption data, and said first updated health related assumption data each comprise assumptions associated with detected medical conditions of said plurality of patients.

12. The computer program product of claim 11, wherein said method further comprises:

executing, by said computer processor based on said first updated health related assumption data, health related actions associated with said plurality of patients.

13. The computer program product of claim 12, wherein said health related actions comprise treatment options for said plurality of patients.

14. The computer program product of claim 13, wherein said health related actions comprises implementing a pay by usage cloud metering model associated with said plurality of patients.

15. The computer program product of claim 12, wherein said method further comprises:

transmitting, by said computer processor to a plurality of health care providers, data describing said health related actions associated with said plurality of patients.

16. The computer program product of claim 11, wherein said previous health related assumption data, said first health related assumption data, and said first updated health related assumption data each comprise assumptions associated with said plurality of patients.

17. The computer program product of claim 11, wherein said generating first updated health related assumption data comprises retracting portions of said first health related assumption data and said previous health related assumption data.

18. The computer program product of claim 17, wherein said method further comprises:

retrieving, by said computer processor, historical patient data and treatment options data;

after said retracting, associating by said computer processor, said first updated health related assumption data with said historical patient data and said treatment options data;

generating, by said computer processor, health related recommendations associated with said plurality of patients; and presenting, by said computer processor via a dashboard view on a display device, said health related recommendations.

19. A computing system comprising a computer processor coupled to a computer-readable memory unit, said memory unit comprising instructions that when executed by the computer processor implements a method comprising:

receiving, by said computer processor from a plurality of data sources, first health event data associated with a first plurality of heath care records associated with a plurality of patients, said computer processor controlling a cloud hosted mediation system comprising an inference engine software application, a truth maintenance system database, and non monotonic logic, wherein said non monotonic logic comprises code for enabling a Dempster Shafer theory;

deriving, by said computer processor executing said inference engine software application, first health related assumption data associated with each portion of portions of said first health event data associated with associated patients of said plurality of patients and related records in said truth maintenance system database, wherein said first health related assumption data comprises multiple sets of assumptions associated with said plurality of patients, wherein each set of said multiple sets comprises assumed medical conditions and an associated plausibility percentage value, wherein at least two sets of said multiple sets is associated with each patient of set plurality of patients, wherein a first set of said multiple sets comprises evidence supporting a first fact indicating that a first patient of said plurality of patients has a first medical condition of said assumed medical conditions with a first plausibility percentage value, wherein a second set of said multiple sets comprises evidence supporting a second fact indicating that said first patient has a second medical condition of said assumed medical conditions with a second plausibility percentage value, wherein said first medical condition differs from said second medical condition, and wherein said first plausibility percentage value differs from said second plausibility percentage value;

determining, by said computer processor, based on results of executing the Dempster Shafer theory with respect to said first set and said second set, that said first set comprises a higher belief assignment value than said second set;

generating, by said computer processor based on results of said determining, said deriving and said first executing, an initial diagnosis and treatment recommendation for said first patient, said initial diagnosis and treatment recommendation associated with said first set;

retrieving, by said computer processor from said truth maintenance system database, previous health related assumption data derived from and associated with previous portions of previous health event data retrieved from said plurality of data sources, said previous health related assumption data derived at a time differing from a time of said deriving, said previous health related event data associated with previous health related events occurring at a different time from said first health event data;

additionally executing, by said computer processor executing said non monotonic logic, the Dempster Shafer theory with respect to said first set, said second set, said first patient, and said previous health related assumption data;

modifying, by said computer processor based on results of said additionally executing, said first plausibility percentage value of said first set and said second plausibility percentage value of said second set;

determining, by said computer processor, based on results of said additionally executing and said modifying, that said second set comprises a higher belief assignment value than said first set;

generating, by said computer processor based on said results of said additionally executing and said modifying, an updated diagnosis and treatment recommendation for said first patient; and generating, by said computer processor executing said non monotonic logic and said inference engine software application, first updated health related assumption data associated with said first health related assumption data and said previous health related assumption data, wherein said previous health related assumption data, said first health related assumption data, and said first updated health related assumption data each comprise assumptions associated with detected medical conditions of said plurality of patients.

* * * * *